US012746111B2

(12) United States Patent
Melles

(10) Patent No.: US 12,746,111 B2
(45) Date of Patent: Sep. 29, 2026

(54) DONOR OVERLAY FOR TREATMENT OR ALLEVIATION OF ANTERIOR CORNEAL DISORDERS

(71) Applicant: NIIOS-USA Inc., San Diego, CA (US)

(72) Inventor: Gerrit Reinold Jacob Melles, Rotterdam (NL)

(73) Assignee: NIIOS-USA INC., San Diego, CA (US)

(*) Notice: Subject to any disclaimer, the term of this patent is extended or adjusted under 35 U.S.C. 154(b) by 1111 days.

(21) Appl. No.: 17/641,595

(22) PCT Filed: Aug. 18, 2020

(86) PCT No.: PCT/IB2020/058724
§ 371 (c)(1),
(2) Date: Mar. 9, 2022

(87) PCT Pub. No.: WO2021/053609
PCT Pub. Date: Mar. 25, 2021

(65) Prior Publication Data

US 2022/0296360 A1 Sep. 22, 2022

(30) Foreign Application Priority Data

Sep. 20, 2019 (EP) .................................... 19198773

(51) Int. Cl.
*A61F 2/14* (2006.01)
*A61L 27/36* (2006.01)

(52) U.S. Cl.
CPC ........ *A61F 2/1451* (2015.04); *A61L 27/3604* (2013.01); *A61L 27/3666* (2013.01); *A61L 27/3691* (2013.01); *A61L 2430/16* (2013.01)

(58) Field of Classification Search
CPC .... A61F 2/1451; A61F 2/142; A61L 27/3604; A61L 27/3666; A61L 27/3691; A61L 2430/16
See application file for complete search history.

(56) References Cited

U.S. PATENT DOCUMENTS 4,662,881 A 5/1987 Nordan
6,544,286 B1 * 4/2003 Perez ................. A61L 27/3683 623/4.1

(Continued)

FOREIGN PATENT DOCUMENTS

| | | | |
|---|---|---|---|
| EP | 1472986 | A1 | 11/2004 |
| WO | 0156379 | A1 | 8/2001 |
| WO | 2009145842 | A2 | 12/2009 |

OTHER PUBLICATIONS

Lie J et al, "Isolated Bowman layer transplantation to manage persistent subepithelial haze after excimer laser surface ablation", Jun. 1, 2010 (Jun. 1, 2010), vol. 36, No. 6, p. 1036-1041, 6 pages.

(Continued)

*Primary Examiner* — Sarah W Aleman
*Assistant Examiner* — Rachel S Highland
(74) *Attorney, Agent, or Firm* — Leason Ellis LLP

(57) ABSTRACT

The invention relates to methods for the treatment or alleviation of an anterior corneal disorder in a subject in need thereof comprising removing corneal epithelial cells from an eye of said subject without removing any corneal tissue or other ocular tissue located posterior to the corneal epithelial cell layer; and positioning an overlay comprising a Bowman layer (BL), Descemet membrane (DM) and/or crystalline lens capsule on the anterior surface of said corneal tissue located posterior to the corneal epithelial cell layer. The invention further relates to freeze-dried and/or gamma irradiated Bowman layer, Descemet membrane and/or crystalline lens capsule and compositions comprising the same that are useful in such methods.

19 Claims, 7 Drawing Sheets

(56) References Cited

U.S. PATENT DOCUMENTS

| | | | | |
|---|---|---|---|---|
| 2003/0105521 | A1 | 6/2003 | Perez | |
| 2014/0155800 | A1* | 6/2014 | de Juan, Jr. .......... | A61F 13/124 602/43 |

OTHER PUBLICATIONS

International Search Report for Corresponding International Application No. PCT/IB2020/058724, dated Nov. 26, 2020. 6 pages.

Groeneveld-van Beek EA, Parker J, Lie JT, Bourgonje V, Ham L, van Dijk K, van der Wees J, Melles GR. "Donor Tissue Preparation for Bowman Layer Transplantation". Cornea. Dec. 2016;35(12):1499-1502.

Lie J, Droutsas K, Ham L, Dapena I, Ververs B, Otten H, van der Wees J, Melles GR. "Isolated Bowman layer transplantation to manage persistent subepithelial haze after excimer laser surface ablation". J Cataract Refract Surg. Jun. 2010;36(6):1036-41.

Parker JS, van Dijk K, Melles GR. "Treatment options for advanced keratoconus: A review". Surv Ophthalmol. Sep.-Oct. 2015;60(5):459-80.

Parker JS, Huls F, Cooper E, Graves P, Groeneveld-van Beek EA, Lie J, Melles GRJ. "Technical feasibility of isolated Bowman layer graft preparation by femtosecond laser: a pilot study". Eur J Ophthalmol. Nov. 8, 2017;27(6):675-677.

Sharma B, Dubey A, Prakash G, Vajpayee RB. "Bowman's layer transplantation: evidence to date. Clin Ophthalmol". Mar. 2018 ; 12:433-437.

Van Dijk K, Parker J, Tong CM, Ham L, Lie JT, Groeneveld-van Beek EA, Melles GR. "Midstromal isolated Bowman ayer graft for reduction of advanced keratoconus: a technique to postpone penetrating or deep anterior lamellar keratoplasty. JAMA Ophthalmol". Apr. 2014; 132(4):495-501.

Van Dijk K, Liarakos VS, Parker J, Ham L, Lie JT, Groeneveld-van Beek EA, Melles GR. "Bowman layer transplantation to reduce and stabilize progressive, advanced keratoconus". Ophthalmology. May 2015;122(5):909-17.

Birbal et al., "Five-year graft survival and clinical outcomes of 500 consecutive cases after Descemet membrane endothelial keratoplasty. ", Cornea 39.3, 2020: pp. 290-297.

Melles et al., "A technique to excise the Descemet membrane from a recipient cornea (descemetorhexis)." Cornea 23.3, 2004: pp. 286-288.

Melles et al. "Descemet membrane endothelial keratoplasty (DMEK)." Cornea 25.8, 2006: pp. 987-990.

Spinozzi et al., "Evaluation of the suitability of biocompatible carriers as artificial transplants using cultured porcine corneal endothelial cells." Current eye research 44.3 ,2019: pp. 243-249.

* cited by examiner

A. Prior published procedure (US 4,662,881)

B. Prior published procedure (US 2003/105521)

C. Prior published procedure (Lie et al. 2010)

D.

C

E

DONOR OVERLAY FOR TREATMENT OR ALLEVIATION OF ANTERIOR CORNEAL DISORDERS

CROSS-REFERENCE TO RELATED PATENT APPLICATIONS

This application is a U.S. National Stage Application under 35 U.S.C. § 371 of International Patent Application No. PCT/IB2020/058724 filed Sep. 18, 2020, which claims the benefit of priority of European Patent Application No. 19198773.4 filed Sep. 20, 2019, both of which are incorporated by reference in their entireties. The International Application was published on Mar. 25, 2021, as International Publication No. WO 2021/053609 A1.

FIELD OF THE INVENTION

The invention relates to the field of ophthalmology, in particular to compositions and tissues for use in eye surgery, especially for treatment or alleviation of anterior corneal disorders.

BACKGROUND OF THE INVENTION

Anterior corneal disorders including corneal curvature disorders and/or corneal contour changes, corneal surface disease, corneal defects, refractive errors of the eye benefit from a surgical procedure that allows for transplantation or implantation of donor corneal tissue, to (partially) restore the corneal anatomy, stability and optical quality, and therefore the visual function of the eye. However, virtually all treatment modalities known today involve sutured fixation of such tissues which in turn is associated with secondary inflammation and all associated risks thereof. Most techniques, including the so-called 'sutureless' techniques are further invasive which may introduce further risk of post-operative complications.

Traditionally, a cornea transplant is a surgical procedure wherein all or part of a damaged cornea is removed and replaced with healthy donor tissue. Several types of cornea transplantation can be performed, i.e. penetrating keratoplasty (PK; full-thickness transplant procedure), deep anterior lamellar keratoplasty (DALK; partial-thickness cornea transplant procedure that involves transplantation of the corneal stroma, leaving the native Descemet membrane and endothelium in place) and endothelial keratoplasty (EK; replacing the posterior layer(s) of the cornea) (Parker et al. 2015).

WO 01/56379 describes a method for treating donor corneal tissue comprising donor stroma with the aim to reduce or prevent corneal graft rejection or an immune or inflammatory response of the eye after corneal transplantation, i.e. replacement of the corneal tissue of the recipient eye with donor tissue.

US 2003/105521 A1 describes the use of a contact lens made of donor corneal tissue, which is acellularized by removing native epithelium and kerotocytes. It is described that the contact lens desirably includes the Bowman layer, but it also includes donor stoma, evidenced by the fact that keratocytes that are present in the stroma are removed from the lens. Before transplantation the lens core is moreover provided with replaced keratocytes and/or replaced epithelial cells covering at least a portion of the anterior surface.

U.S. Pat. No. 4,662,881 describes grafting of a donor cornea shaped into a lenticle to the front of a patient's cornea. The edge of the donor cornea is inserted into peripheral corneal grooves cut into the patient's cornea and then sutured to the patient's cornea (referred to as an epikeratophakia operation).

Recently, transplantation of a Bowman layer has been reported for the surgical treatment of keratoconus (KC) and a similar procedure has been reported for treatment of post-laser surface complications of the eye and persistent subepithelial haze after excimer laser surface ablation (Sharma et al. 2018; Van Dijk et al. 2015, Lie et al. 2010). This procedure involves transplantation of donor Bowman layer into the mid-stroma of the cornea. Although such procedure is associated with less intraoperative and postoperative complications as compared to previously used techniques, the procedure remains of an invasive nature involving the creation of a mid-stromal pocket in the recipient cornea. In addition, the technique is surgically complex and prone to corneal perforation during surgery. Lie et al. 2010 describes that the isolated Bowman layer transplantation was carried out to avoid an epithelial-stromal wound-healing response, thereby preventing or minimizing the formation of subepithelial scar tissue induced by epithelial-stromal interaction.

Hence, there remains a need in the art for improved means and methods for treatment and alleviation of corneal curvature disorders, that address one or more of the drawbacks of the current procedures.

SUMMARY OF THE INVENTION

It is an object of the present invention to provide improved means and methods for treatment or alleviation of anterior corneal disorders, which involve applying donor corneal tissue to a recipient eye, and which methods are less invasive than current methods and can preferably be performed sutureless.

The invention therefore provides a method for the treatment or alleviation of an anterior corneal disorder in a subject in need thereof, the method comprising:

- removing corneal epithelial cells from an eye of said subject without removing any corneal or other ocular tissue located posterior to the corneal epithelial cell layer; and
- positioning an overlay comprising a Bowman layer (BL), Descemet membrane (DM) and/or crystalline lens capsule on the anterior surface of said corneal tissue located posterior to the corneal epithelial cell layer. It will be understood by the skilled person that the overlay is positioned on the anterior surface of said corneal tissue located posterior to the corneal epithelial cells that have been removed in the first step. As detailed herein below, these corneal epithelial cells that are removed will later be restored.

In a further aspect, the invention provides an overlay comprising a Bowman layer (BL), Descemet membrane (DM) and/or crystalline lens capsule for use in a method for the treatment or alleviation of an anterior corneal disorder in a subject, wherein said method comprises:

- removing corneal epithelial cells from an eye of said subject without removing any corneal or other ocular tissue located posterior to the corneal epithelial cell layer; and
- positioning said overlay on the anterior surface of said corneal tissue located posterior to the corneal epithelial cell layer.

In a further aspect, the invention provides a method for inducing a tissue remodeling response in the corneal stroma of a subject, wherein said corneal stroma comprises scar tissue associated with or resulting from an anterior corneal disorder, the method comprising:

removing corneal epithelial cells from an eye of said subject without removing any corneal tissue or other ocular tissue located posterior to the corneal epithelial cell layer; and positioning an overlay composed of a Bowman layer (BL) or composed of more than one layer, wherein each layer is composed of a BL, on the anterior surface of said corneal tissue located posterior to the corneal epithelial cell layer. In one embodiment, the subject is suffering from said anterior corneal disorder.

In a further aspect, the invention provides an overlay composed of a Bowman layer (BL) or composed of more than one layer, wherein each layer is composed of a BL, for use in a method for inducing a tissue remodeling response in the corneal stroma of a subject, wherein said corneal stroma comprises scar tissue associated with or resulting from an anterior corneal disorder, and wherein said method comprises:

removing corneal epithelial cells from an eye of said subject without removing any corneal or other ocular tissue located posterior to the corneal epithelial cell layer; and positioning said overlay on the anterior surface of said corneal tissue located posterior to the corneal epithelial cell layer. In one embodiment, the subject is suffering from said anterior corneal disorder.

In a further aspect, the invention provides a use of a Bowman layer (BL), Descemet's membrane (DM) and/or crystalline lens capsule in the preparation of an overlay for the treatment or alleviation of an anterior corneal disorder in a subject, wherein said method comprises:

removing corneal epithelial cells from an eye of said subject without removing any corneal or other ocular tissue located posterior to the corneal epithelial cell layer; and positioning the overlay comprising a BL, DM and/or crystalline lens capsule on the anterior surface of said corneal tissue located posterior to the corneal epithelial cell layer.

In a further aspect, the invention provides a freeze-dried and/or gamma irradiated BL, DM and/or crystalline lens capsule.

In a further aspect, the invention provides a composition, or overlay, comprising more than one layer, wherein each layer independently comprises a BL, DM or crystalline lens capsule, preferably wherein at least one layer comprises a BL. In a preferred embodiment, the composition is composed of said more than one layer. In a particularly preferred embodiment, all layers of a composition according to the invention are BLs. It is further preferred embodiment, the composition or the BL, DM and/or crystalline lens capsule are freeze-dried and/or gamma-irradiated.

In a further aspect, the invention provides a method for inducing a tissue remodeling response in the corneal stroma of a subject, wherein said corneal stroma comprises scar tissue associated with or resulting from an anterior corneal disorder, the method comprising:

removing corneal epithelial cells from an eye of said subject without removing any corneal tissue or other ocular tissue located posterior to the corneal epithelial cell layer; and positioning a composition according to the invention comprising more than one layer, wherein each layer independently comprises a BL, DM or crystalline lens capsule, preferably wherein at least one layer comprises a BL, on the anterior surface of said corneal tissue located posterior to the corneal epithelial cell layer.

In a further aspect, the invention provides a composition according to the invention comprising more than one layer, wherein each layer independently comprises a BL, DM or crystalline lens capsule, preferably wherein at least one layer comprises a BL, for use in a method for inducing a tissue remodeling response in the corneal stroma of a subject, wherein said corneal stroma comprises scar tissue associated with or resulting from an anterior corneal disorder, and wherein said method comprises:

removing corneal epithelial cells from an eye of said subject without removing any corneal or other ocular tissue located posterior to the corneal epithelial cell layer; and positioning said overlay on the anterior surface of said corneal tissue located posterior to the corneal epithelial cell layer.

In a further aspect, the invention provides a freeze-dried and/or gamma irradiated BL, DM and/or crystalline lens capsule or composition according to the invention for use in therapy.

In a further aspect, the invention provides a freeze-dried and/or gamma irradiated BL, DM and/or crystalline lens capsule or composition according to the invention for use in a method for the treatment or alleviation of an anterior corneal disorder in a subject, wherein said method comprises:

removing corneal epithelial cells from an eye of said subject without removing any corneal or other ocular tissues located posterior to the corneal epithelial cell layer; and positioning BL, DM or crystalline lens capsule or composition according to the invention on the anterior surface of said corneal tissue located posterior to the corneal epithelial cell layer.

In a further aspect, the invention provides a method for the treatment or alleviation of an anterior corneal disorder in a subject in need thereof, the method comprising:

removing corneal epithelial cells from an eye of said subject without removing any corneal or other ocular tissues located posterior to the corneal epithelial cell layer; and positioning a freeze-dried and/or gamma irradiated BL, DM or crystalline lens capsule or composition according to the invention on the anterior surface of said corneal tissue located posterior to the corneal epithelial cell layer.

DETAILED DESCRIPTION

The present inventor surprisingly recognized that a wide range of anterior corneal disorders (corneal curvature disorders, corneal instability, corneal wound healing disorders, corneal defects, melts, peripheral thinning and surface irregularities, various forms of ocular surface disease, and refractive errors of the eye) can be treated by positioning an isolated donor BL, DM and/or crystalline lens capsule onto the recipient anatomical BL of the normal living eye (after epithelial debridement). To this end a technique has been developed in which a donor BL can be positioned underneath the corneal epithelium, at the level of or onto the existing host BL or when the recipient BL is absent, onto the most anterior stromal layers. As part of the technique, various methods have been developed to surgically dissect, preserve and store a BL from a human donor cornea.

FIG. 1 shows a comparison of prior published procedures and the procedure of the present invention.

Lie et al. 2010 showed that an isolated donor Bowman layer can be positioned on top of the cornea after removal of the patient's own Bowman layer. The isolated Bowman layer transplantation was carried out to avoid an epithelial-stromal wound-healing response.

A key issue with any type of donor tissue placed on the corneal tissue of the eye of a patient is the lack of wound healing between donor corneal stroma and a host (patient) Bowman layer. Since wound healing does not occur between these tissues, at least not to any clinically useful extent, various types of donor corneal tissues positioned onto the patient's Bowman layer, remains 'loose' and is therefore at risk to dislocate or come off of the cornea. For that reason, any type of epikeratoplasty was therefore fixed with sutures, while the edge of the transplant (consisting mainly of donor stroma with its Bowman layer on top) was 'tucked in' after circular trephination, as described in U.S. Pat. No. 4,662,881 (see FIG. 5 of U.S. Pat. No. 4,662,881). In other words, a donor stromal to host stromal contact was created to enable wound healing and long term fixation after suture removal (FIG. 1A).

The problem of long term fixation through wound healing is further illustrated by US 2003/105521 A1. It is described that a "pre-fabricated ocular contact lens ( . . . ) of donor corneal tissue" is "devitalized" (removal of cells) and that the absent stromal cells in the donor tissue are replaced by host stromal cells: " . . . the stroma portion of the lens core is repopulated with [host] keratocytes". For an influx of stromal cells (keratocytes) to occur, there must be stromal-to-stromal contact (i.e. between the donor and host stroma), since the Bowman layer of the recipient is an impermeable barrier to both stromal and epithelial cells. In other words, although it is technically possible to position a graft onto the cornea that is subsequently covered by host epithelium, a major drawback of this technique is still the risk of graft dislocation after minor trauma (since there is no wound healing response between the stromal graft surface and the underlying host Bowman layer) (FIG. 1B).

Interestingly, direct stromal contact between the corneal epithelial layer and the stroma, for example after photorefractive keratectomy (PRK; removal of Bowman layer and superficial stroma to change the curvature of the cornea and therefore the refractive error of the eye), frequently results in scar tissue formation at the interface, referred to as 'stromal haze'. Excessive haze may occur in a relatively low percentage of post-PRK eyes, which may cause a significant drop in visual acuity. To manage post-PRK eyes with grade 4 haze, the present inventor previously exploited the fact that scarring does not occur at a stroma-to-Bowman layer interface, by removing the scar tissue and positioning an isolated donor Bowman layer on top of the denuded stroma from which the Bowman layer has been removed, to again create a barrier between the epithelium and stroma, as described in Jie et al. 2010 (FIG. 1C). However, this approach did not solve the issue of tissue fixation, since lack of wound healing between donor and host tissues was advantageous from a visual acuity perspective (no scarring, therefore no recurrent haze), but ineffective due to lack of wound healing induced fixation and the resulting risk of dislocation.

To overcome the lack of a sufficient wound healing response, the inventor now shows the use of an isolated donor Bowman layer (i.e. a Bowman layer graft devoid of donor stroma) positioned onto the patient's anatomical Bowman layer, since it was hypothesized that it was the donor stroma that interfered with or blocked the wound healing response between a Bowman layer and stromal tissues. In other words, if an (isolated) Bowman layer graft is positioned onto the patient's own Bowman layer (FIG. 1D and FIG. 4), a different type of wound healing response is elicited by a mechanism that is hypothesized not to involve keratocytes, but inflammatory cells derived from the tear film. The wound healing induces tissue contraction and fixation, but also remodeling of the central cornea resulting in improved central corneal clarity.

In addition to the wound healing process observed at the (donor) BL—(host) BL interface, a different wound healing response is observed in the (host) stromal tissue. Stromal scar tissue, that usually presents as a white opacification in the cornea, shows virtually complete repair and remodeling when an overlay or composition according to the present invention is positioned on the recipient BL. Such pre-existing scar tissue, results from a long standing disorder and/or underlying disease, such as a post-infectious scar after Herpes keratitis or bacterial ulcer, advanced keratoconus, ocular trauma, or any other condition affecting the anatomical structure of the cornea. As can be seen in FIGS. 4 and 5 herein, such opacities disappear following the performance of a procedure according to the present invention resulting in a recovery and/or repair of the stromal tissue, that is a remodeling towards a normal stromal tissue structure. In currently used procedures, which involve transplantation or implantation of donor corneal tissue, the scar tissue in the stromal tissue is usually surgically removed and replaced by donor tissue. The present inventor has shown that, when using a procedure according to the present invention, surgical removal of such stromal scar tissue caused by corneal disorder, is unnecessary. As a result, the risk of complications of the intervention is greatly reduced (no suture-related complications, no allograft rejection, minimal risk of intraocular complications) while the visual recovery is often faster and more complete.

Hence, the present overlay induces two types of wound healing responses: 1) a moderate wound healing response at the BL-BL interface, and 2) a tissue remodeling response in the underlying corneal stroma. The presence of a BL graft avoids scar tissue formation and 'stromal haze', that is induced with excessive wound healing. Sufficient wound healing between the donor and host Bowman layers is mandatory in most types of treatment with donor corneal tissue, and in particular with anterior corneal disorders such as keratoconus, an ectasia of the corneal contour. Not only to fix the donor tissue on the recipient corneal tissue, but also in order to reduce the corneal contour and to improve visual acuity. The wound healing response at the interface between the donor and host Bowman layers as well as subsequent 'wound contraction' exerted by the donor tissue aids in flattening the corneal curvature, while providing sufficient tensile strength to halt progression of a keratoconic cornea by maintaining the corneal shape in the long term. In addition, a wound healing response is induced in scar tissue in the recipient stroma resulting in repair of such scar tissue and further improvement of clinical outcomes.

The technique of the present invention has proven to give far less trauma to the patient, especially since the host cornea tissue is not structurally altered, the anterior and posterior corneal surface are not compromised, the procedure is largely 'reversible', and the entire intervention does not require entry into the anterior chamber of the eye or any intraocular manipulation. In fact, the approach may be considered 'non-invasive' since none of the tissue layers is incised or structurally altered; removal of the anterior corneal surface epithelium is known to show quick restoration of the epithelial cell layer.

The present invention is directed to a method for the treatment or alleviation of an anterior corneal disorder in a subject in need thereof, the method comprising:

removing corneal epithelial cells from an eye of said subject without removing any corneal or other ocular tissues located posterior to the corneal epithelial cell layer; and positioning an overlay comprising a BL, DM and/or crystalline lens capsule on the anterior surface of said corneal tissue located posterior to the corneal epithelial cell layer.

The invention is further directed to a method for inducing a tissue remodeling response in the corneal stroma of a subject, wherein said corneal stroma comprises scar tissue associated with or resulting from an anterior corneal disorder, the method comprising:

removing corneal epithelial cells from an eye of said subject without removing any corneal tissue or other ocular tissue located posterior to the corneal epithelial cell layer; and positioning an overlay composed of a Bowman layer (BL) or composed of more than one layer, wherein each layer is composed of a BL, on the anterior surface of said corneal tissue located posterior to the corneal epithelial cell layer.

The invention is further directed to a freeze-dried and/or gamma irradiated BL, DM and/or crystalline lens capsule, preferably a fresh, cultured, freeze-dried BL. In currently used methods of transplantation of corneal tissue or implantation of a BL in the corneal stroma the donor tissue is routinely stored in organ culture medium to be useful in such procedures. However, it is now possible to store the BL in various wet, but also dry forms, e.g. in fresh, cultured, freeze-dried form or after gamma-irradiation or a combination thereof. Such treatment of the donor tissue is described in more detail herein below.

Also provided is a composition comprising more than one layer, wherein each layer independently comprises a freeze-dried and/or gamma irradiated BL, DM or crystalline lens capsule according to the invention. Such, BL, DM or crystalline lens capsule or composition according to the invention can advantageously be used in a method for the treatment or alleviation of an anterior corneal disorder according to the invention. In a preferred embodiment, the composition is comped of more than one layer. In a further preferred embodiment, the composition consists of said more than one layer.

As used herein, the term "subject" or "recipient subject" encompasses humans but also animals that show disorders as detailed herein similar to humans, preferably mammals. Preferably, a subject or recipient subject is a mammal, more preferably a human. In a particular embodiment, a subject is suffering from an anterior corneal disorder, preferably selected from the group consisting of a corneal curvature disorder, a corneal instability disorder, a corneal wound healing disorder, a corneal surface disorder, a corneal defect, melt or peripheral thinning, an ocular surface disease and a refractive error of the eye.

As used herein, the terms "treatment," "treat," and "treating" refer to reversing, alleviating, delaying the onset of, or inhibiting the progress of an anterior corneal disorder, or one or more symptoms thereof. In some embodiments, treatment may be administered after one or more symptoms have developed. In other embodiments, treatment may be administered in the absence of symptoms, after diagnosis has been performed indicating that the subject is suffering from or at risk of suffering from an anterior corneal disorder.

The terms "anterior" and "posterior" are well known in the art of eye surgery and ophthalmology. Anterior refers to the front side of a tissue structure or ocular element, while posterior refers to the rear side of such structures or elements.

As used herein "corneal tissue" refers to any part or parts of the cornea, i.e. epithelium, BL, stroma, DM and endothelium. The term "any corneal tissue located posterior to the corneal epithelial cell layer" refers to any corneal tissue except the epithelium, i.e. to BL, stroma, DM and endothelium.

As used herein the term "overlay" refers to a donor material comprising a BL, DM and/or crystalline lens capsule and that, in accordance with the method of the present invention, can be placed on top of a BL of the recipient eye or part thereof, or in the absence of Bowman's layer on top of the anterior corneal stroma.

As used herein, the term "independently" in the context of a composition according to the invention means that each layer of the composition can be a BL, a DM or a crystalline lens capsule, i.e. the layers can be different. It is not necessary that all layer are the same, i.e. that the layers are BLs or all layer are DMs or all layers are crystalline lens capsules. However, in a preferred embodiment, all layers of the composition are either BLs, DMs or crystalline lens capsules. In a particularly preferred embodiment, all layers of a composition according to the invention are BLs.

The cornea is the transparent most anterior part of the eye that covers the iris, pupil, and anterior chamber. The cornea refracts light, together with the lens, and as a result aids in focusing. It accounts for approximately two-thirds of the eye's total optical power. The human cornea consist of five distinct layers, the epithelium, Bowman layer, stroma, Descemet membrane and endothelium.

The BL (also referred to as Bowman membrane, anterior limiting lamina and anterior elastic lamina) is an acellular layer, composed of strong, randomly oriented collagen fibrils, mainly type I collagen, but also types III, V and VI. The smooth anterior surface of the BL faces the epithelium and the posterior surface merges with the collagen lamellae of the corneal stroma. In adult humans, BL is typically 8-12 μm thick, but it may become thicker or thinner with ageing.

The Descemet membrane is the membrane that lies between the corneal stroma and the endothelial layer of the cornea and is also composed of collagen, mainly type IV and VIII collagen.

The crystalline lens capsule refers to the acellular outer covering of the crystalline lens of the eye, composed of collagen fibrils embedded in a glycosaminoglycan matrix.

In a preferred embodiment, the treatment or alleviation comprises inducing a wound healing response at the interface between said overlay and Bowman layer of the subject. In a further preferred embodiment, the treatment or alleviation comprises inducing a tissue remodeling response in the corneal stroma of the subject. A "tissue remodeling response" as used herein refers to the remodeling of stromal scar tissue associated with or resulting from the anterior corneal disorder. "Remodeling" as used herein refers to mitigation and/or disappearance of stromal scar tissue. I.e. remodeling of stromal scar tissue to healthy stromal tissue. Such stromal scar tissue usually presents as a white opacification that is visible in the cornea.

The overlay used in accordance with the invention or composition according to the invention may be single- or multi-layered, i.e. it may comprise a single BL, DM or crystalline lens capsule, multiple BLs, DMs or crystalline lens capsules or a combination of one or more BLs, one or more DMs and/or one or more crystalline lens capsules, preferably donor BL(s), DM(s) and/or crystalline lens capsule(s). In one preferred embodiment, the overlay is composed of a single BL, DM or crystalline lens capsule, preferably a single BL. In another preferred embodiment, the overlay is composed of more than one layer, wherein each layer is composed of a single BL, DM or crystalline lens capsule, preferably a single BL. In a preferred embodiment, the overlay or composition comprises one or more BLs or one or more DMs, more preferably one or more BLs. In a particularly preferred embodiment, the overlay or composition comprises one or more BLs as the sole donor eye tissue, but may comprise further substances such as one or more dyes and/or riboflavin or other adjuvants that facilitate visualization of the overlay, or active component, e.g. any active component used in treatment of the eye, in particular disorder of the eye. In a further preferred embodiment, the overlay consists of one or more donor BLs, optionally with one or more dyes, preferably one or more vital dyes as described herein below. Further, the composition preferably consists of more than one donor BL, optionally with one or more dyes, preferably one or more vital dyes as described herein below. The one or more BL, DM or crystalline lens capsules may further be derived from the same of different donors. The donor material (BL, DM or crystalline lens capsule, preferably BL) may be derived from one or more human donors, but this is not necessary. The source of the donor tissue is preferably human to comply to regulatory guidelines, but tissue from other species were found to be equally effective. Any animal eye that contains a BL, DM or crystalline lens capsule, respectively, can be used as donor material. For instance, multiple animals, including mammals and birds such as or other bovines, horses and other equus, dogs and other canines and ostrich contain a BL in the cornea, whereas e.g. cats and swines do not. In a preferred embodiment, the donor material, preferably donor BL, is thus human or animal, derived from an animal the cornea of which contains a BL. In a particularly preferred embodiment, the donor material, preferably the one or more donor BLs is or are selected from the group consisting of human or animal donor material, preferably BL or BLs.

An adult human BL has an average thickness of 8-12 μm and an adult DM has an average thickness of 5-10 μm. Hence it is preferred that the overlay or composition according to the invention has an average thickness of at least about 5 μm, more preferably at least 7 μm, more preferably at least 8 μm, more preferably at least about 10 μm. The human cornea has an average thickness of about 500 μm, which if the recipient has a large defect, could be essentially replaced by the overlay or composition with a method of the invention. The overlay or composition thus preferably has an average thickness of at most 600 μm, preferably at most 550 μm, more preferably at most 500 μm. The overlay or composition preferably has an average thickness of 5-600 μm, preferably 8-550 μm, more preferably 10-500 μm, more preferably 10-250 μm, more preferably 10-150 μm, more preferably 10-100 μm, more preferably 10-50 μm. The thickness of the overlay or composition may depend on the type of disorder treated. "Average thickness" refers to a layer (i.e. the overlay or composition), where the layer where the thickness may vary from one region of the layer to another region of the layer and the average thickness is the average of the various thicknesses of the regions of the layer. The average thickness of an overlay or composition according to or used in accordance with the invention can be measured using any suitable method known in the art, such as light microscopy, ultrasound, tomography, etc. It can for instance be determined by measuring and averaging the thickness at e.g. 3 spots across the overlay or composition.

The overlay or composition according to the invention further preferably has an average diameter of 1-12 mm, more preferably of 2-12 mm, more preferably of 3-12 mm, more preferably of 4-12 mm, more preferably of 5-12 mm, more preferably of 6-12 mm, more preferably of 8-12 mm. In a further preferred embodiment, the average diameter of the overlay is 8-9 mm. The term "average diameter" refers to the average diameter of the surface of the overlay or composition that is aligned with the corneal tissue of the recipient eye, preferably the recipient BL. It further refers to the average of the sum of greater axis and smaller axis dimensions. The overlay used in accordance with the invention or composition according to the invention preferably has a circular or cylindrical, oval or elliptical shape, more preferably a circular shape. Preferably, the diameter of a circular shaped overlay or composition is essentially uniform, with a deviation of up to 1 up to 50%. The diameter of the overlay or composition, which lies within the visible range, can be easily determined across the edge of the overlay or composition using any suitable measuring equipment known in the art. In a particularly preferred embodiment the overlay or composition according to or used in accordance with the invention is circular, resulting from the BL, DM or crystalline lens capsule being punched or cut, e.g. with a trephine, laser, or knife to the desired diameter.

A BL in the healthy eye has a dome shape with a curvature of approximately 43 diopter (range 36 to 50 diopter). Fixation of the overlay or composition according to the invention may reduce the curvature of the underlying recipient cornea to the intrinsic BL curvature, or reduce the curvature of the recipient corneal curvature towards a normal corneal curvature. Fixation of the curvature of the overlay or composition can for instance be achieved by shaping the overlay or composition shortly after it has been positioned on the eye, in particular during the time period that the overlay or composition is allowed to dry in. Hence, in a preferred embodiment, an overlay or composition according to the invention or used in accordance with the invention, preferably comprising or composed of one or more layers of BL, preferably has a curvature of about 36 to 50 diopter.

A method according to the present invention comprises removing corneal epithelial cells from an eye of said subject. It is preferred that essentially all corneal epithelial cells of the part of the cornea that will be covered by the overlay or composition according to the invention are removed prior to positioning the overlay or composition on the anterior surface of the corneal tissue located posterior of to the (removed) epithelial cells. However, a small number of residual epithelial cells will not hamper attachment of the overlay or composition to the anterior surface of the corneal tissue. In addition, epithelial cells covering part of the cornea that will not be covered by the overlay or composition do not need to be removed. Hence, in a preferred embodiment at least 80% of corneal epithelial cells covering the part of the anterior surface of the corneal tissue that will be covered by the overlay or composition according to the invention is removed from the eye of the recipient subject. I.e. if the overlay or composition, after treatment in accordance with the invention, will cover 70% of the surface of the corneal tissue located posterior to the epithelial cell layer it is preferred that at least 80% of the epithelial cells covering said 70% of the surface of the corneal tissue located posterior to the epithelial cell layer is removed. More preferably at least 85% of corneal epithelial cells covering the part of the anterior surface of the corneal tissue that will be covered by the overlay or composition according to the invention, more preferably at least 90% of, more preferably at least 95%, more preferably at least 97%, more preferably at least 98%, more preferably at least 99%. In a particularly preferred embodiment, essentially all corneal epithelial cells or all corneal epithelial cells covering the part of the anterior surface of the corneal tissue that will be covered by the overlay or composition according to the invention are removed. Following placement of the overlay or composition, the recipient eye will restore the corneal epithelial cell layer, typically within a couple of weeks after the procedure.

A method according to the present invention comprises removing corneal epithelial cells from an eye of said subject without removing corneal tissue located posterior to the corneal epithelial cell layer. The present inventors indeed surprisingly found that the overlay as defined herein can be placed over the eye of a patient from which only the anterior epithelial cells have been removed, without the need to remove further corneal or other eye tissue of the recipient eye. In a preferred embodiment, a method or use according to the invention does not entail removal of BL, stromal tissue, DM or corneal endothelium from the recipient cornea. In contrast, any currently known method of treatment using donor corneal tissue, such as a BL, concerns either transplantation (i.e. replacement of the corneal tissue of the recipient eye with donor tissue) or implantation (i.e. placement of the donor tissue into the stroma, instead of onto the surface of the cornea). The first layer of the cornea posterior to the corneal epithelial cell layer is the BL. If the recipient eye contains an intact BL, part of an BL or damaged BL, the overlay or composition according to the invention is positioned on top of the intact, partial or damaged BL. If the cornea of the recipient eye does not have a BL, i.e. the BL was absent prior to removal of epithelial cells, the overlay or composition is positioned on top of the corneal tissue that is present in the recipient eye, e.g. stromal corneal tissue or DM, most likely stromal tissue.

Corneal tissue located posterior to the corneal epithelial cell layer of the cornea on which the overlay or composition is positioned preferably comprises at least part of a BL and anterior corneal stromal tissue or, where the cornea of the subject lacks a BL, said corneal tissue located posterior to the corneal epithelial cell layer comprises anterior corneal stroma. Preferably, said corneal tissue located posterior of to the corneal epithelial cell layer comprises at least part of a BL and anterior corneal stromal tissue. Hence, the cornea of the recipient preferably comprises at least part of a BL. Preferably said part comprises at least 10% of an intact Bowman's layer, more preferably at least 20%, more preferably at least 30%, more preferably at least 40%, more preferably at least 50%. As used herein, "part of a BL" refers to the presence of a damaged BL, whereby the size, shape or thickness of the BL is altered as compared to an intact BL. Damage to an BL may for instance be a result of an anterior corneal disorder.

Methods to remove a BL, DM or crystalline lens capsule are well known in the art.

A BL can be selectively removed from a human or animal donor cornea, without removing part of the directly underlying anterior corneal stroma. After removal of the surface epithelial layer, any forceps and/or knife or similar instrument may be used to lift a peripheral edge of BL at the 'BL-stroma dissection plane'. After the BL is loosened first at the periphery, it can then be pulled gently toward the central cornea, stripping it from the corneal stroma, by peeling it over 360 degrees. Alternatively, a BL can be manually dissected with various spatulas, or mechanically with a femtosecond laser, Nd:YAG laser or other means to disrupt the anchoring fibrils between Bowman layer and the underlying, anterior stroma. Suitable methods for removal of donor BL are described in Van Dijk et al. 2014, Van Dijk et al. 2015, Lie et al. 2010, Groeneveld-van Beek et al. 2016, Parker et al. 2017.

A DM can be harvested from a human or animal cornea using methods known in the art, for instance as part of a Descemet Membrane Endothelial Keratoplasty (DMEK), and can be performed for instance by a technician in an eye bank or during surgery by a surgeon. Suitable methods are described in Melles et al. 2004, Melles et al. 2006 and Birbal et al. 2019.

A crystalline lens capsule can be harvested from a human or animal cornea methods known in the art. A suitable method is described in Spinozzi et al. 2019.

The dissection of the donor BL, DM or crystalline lens capsule is facilitated by 'ageing' the donor tissue by subjecting it to various steps, including but not limited to hypo- and hyperthermic media, freezing and thawing, air and/or Balanced Salt Solution (BSS) injection into the anterior stroma, enzymatic solutions, and/or prolonged storage. The tip being angled relative to the intermediate part allows The dissection may be performed on a whole globe (intact human donor eye) that is positioned in an globe holder with a suction device. Alternatively, a corneo-scleral rim may be mounted on epithelial side up in a holder, so that the BL can also be dissected from corneo-scleral rims. After dissection, the BL sheet is preferably emerged in ethanol 90% and punched with a trephine to the desired diameter, usually 6-12 mm and more preferably 8-9 mm graft size.

Following isolation of the donor tissue, it can be directly used in a method according to the invention or it can be stored prior to being used in such method. To store the tissue, preferably the donor tissue, preferably BL, can be submerged in a liquid medium, protecting said tissue and leading to the effect that the BL or DM will roll up by itself. Such a liquid can comprise of Balanced Salt Solution (BSS), an organ culture medium, or a combination thereof, with or without antibiotic and antifungal agents. Alternatively, the dissected Bowman layer can be stored dry or be frozen with or without protective agents (eg. glycerol). The tissue may also be subjected to sterilization steps, for example gamma irradiation. In one embodiment, therefore, the overlay or composition has been subjected to drying, freeze-drying or gamma irradiation prior to positioning it on the anterior surface of the corneal tissue located posterior of to the (partially) removed epithelial cell layer. Freeze-drying is a procedure well known in the art and is for instance performed by freezing donor tissue, overlay or composition, e.g. at −20° C., −40° C. or −70° C., followed by drying for e.g. 10-24 hours such as 12 hours, optionally under reduced pressure. The freeze-dried donor tissue, overlay or composition is then preferably stored at a temperature below 0° C., e.g. at −20° C., −40° C. or −70° C. Gamma irradiation can be performed by subjecting the donor tissue, overlay or composition in any suitable gamma irradiating facility. The material can subsequently be dry stored at temperatures above 0° C., preferably at about room temperature. In the case of a multi-layered overlay or composition, it is preferred that each BL, DM or crystalline lens capsule layer is individually treated and stored and that the multi-layered overlay or composition is prepared from multiple individually stored BL, DM or crystalline lens capsule layers prior to positioning it on the recipient corneal tissue, e.g. 0-2 hours prior thereto.

Multiple layers of BL, DM and/or crystalline lens capsule, preferably multiple layers of BL, can be combined at any moment to provide a multi-layered overlay or composition according to the invention, e.g. after harvesting the different layers from multiple donor eyes and prior to storing, after storing of each layer individually and shortly before performing a method according to the invention, or multiple layer are combined after storing of each layer individually and subsequently stored again as a multilayered overlay or composition before this is used in a method according to the invention. The different layers can be combined into a composition according to the invention and allowed to dry in, e.g. for 30-120 minutes. Alternatively, the multiple layers are combined and crosslinked, preferably with riboflavin, e.g. for 5-60 minutes, or heated for e.g. 1-30 minutes at 40-60° C. or 1-30 seconds at 60-80° C. The overlay or composition can subsequently be used directly in a method according to the invention or stored fresh, in organ culture medium, freeze-dried, be gamma irradiated or a combination thereof. Overlays or compositions isolated and treated as described herein can be stored for long periods of time, e.g. up to multiple years.

Prior to positioning the overlay or composition according to the invention on the recipient eye, it may be stained in order to enhance visualization during the surgical procedure. Hence, in a preferred embodiment, the overlay or composition according to, or used in accordance with, the invention is stained before said overlay of composition is positioned on the anterior surface of said corneal tissue located posterior to the corneal epithelial cell layer. Staining is preferably with a vital dye or a combination of vital dyes. The term "vital dye" as used herein refers to a dye which has a sufficient coloring, or staining capacity at a concentration which is physiologically and toxicologically acceptable (e.g. without clinically significant interference with the cell metabolism). Hence, such a dye can be used in an (in-vivo) environment of living cells and tissues. In other words, the minimum amount of dye which is necessary to provide sufficient staining for a useful coloring to be visible should be low to such an extent that no, or hardly any, adverse toxic effects occur. Preferably, the dye is trypan blue or another di-azo vital dye, preferably selected from the group consisting of azafloxin, basic blue (nil blue sulphate), bismarck brown, basic red (rhodamine 6G), bengal red, brillant crysyl blue, eosin, fluorescein, gentian violet, indocyanine green, methylene green, methylene blue, neutral red, trypan blue, and trypan red, Chicago Sky blue 6B, 2-naphtol orange, Allura Red AC, Diamine Green B, Fast Yellow AB, and Janus Green B, 2-naphtol orange, Allura Red AC, Fast Yellow A and combinations thereof. It has been found that these dyes provide a clearly visible staining at very low amounts. Also, they have an advantageous toxicity profile. Suitable vital dyes are further described in WO 99/58159, WO 99/58160, WO 2011/122947 and PCT/NL2019/050265. A particularly preferred dye is trypan blue (TB). Staining of the BL, DM, crystalline lens capsule or overlay or composition according to the invention may for instance be performed by submerging the tissue in a liquid staining composition comprising the dye or combination of dyes, in particular an aqueous staining composition. For example, a liquid staining composition may comprise 0.001-0.3 wt. % of the dye or combination of dyes, preferably 0.01 to 0.1% wt. %. Preferably, the staining composition comprises 0.001-0.3 wt. % TB, preferably 0.01 to 0.1% wt. % TB. The staining composition may comprise further components such as a salt (e.g. sodium chloride, potassium chloride, calcium chloride, magnesium chloride, or a combination thereof), so that the composition is preferably isotonic with ocular fluid and having a osmolarity between 250 and 400 mosmol/L, and/or a viscosity increasing compound such as polyethylene glycol.

In one preferred embodiment, the BL, DM or crystalline lens capsule, the overlay for use according to the invention, the composition according to the invention or one or more layers of a composition according to the invention is treated with an active component. Any active component that is known to be useful in treatment of disorders of the eye can be used. Preferred examples of active components are stromal growth factors and epithelial growth factors. Stromal growth factors and epithelial growth factors used in the eye are well known to a person skilled in the art and can be suitably used in the methods of the present invention. As used herein "treated with" means that the active components has been contacted with or added to the BL, DM or crystalline lens capsule, the overlay for use according to the invention, the composition according to the invention or one or more layers of a composition according to the invention. For instance, the BL, DM or crystalline lens capsule, the overlay for use according to the invention, the composition according to the invention or one or more layers of a composition according to the invention is provided with the active component in a suitable solvent, preferably an aqueous or oil-based solution, e.g. by soaking the BL, DM or crystalline lens capsule, the overlay for use according to the invention, the composition according to the invention or one or more layers of a composition according to the invention in said solvent. Alternatively, the active component, preferably stromal growth factor or epithelial growth factor, is applied to the eye after positioning of the overlay or composition in the form of e.g. eyedrops.

A method according to the invention can be performed as follows. From the host cornea, corneal epithelium is carefully removed to denude the recipient BL or in absence thereof, the anterior corneal stroma. The epithelium can for instance be removed by spatula abrasion under topical anesthesia. Pre-dissected donor tissue (preferably BL) at any diameter and either directly after harvesting or after having been stored by any of the methods mentioned above, are removed from the sterile vial, container and/or seal. The donor tissue is then first rehydrated, for example with BSS, and preferably stained with a vital dye as described herein above. The assembly of an multi-layered overlay is preferably performed in an eye bank, for instance. as described herein above, but in the case of a multi-layered overlay or composition according to the invention, the different layers of donor tissue can also be combined during or as part of the surgical procedure itself, preferably after rehydration and either before or after staining with a vital dye. An advantage of a surgical method of the invention is that it is not necessary to suture the overlay or composition onto or into tissue of the eye of the recipient. Hence, in a preferred embodiment, the overlay or composition is positioned sutureless on the corneal tissue of the recipient subject. The overlay or composition is thus positioned onto the cornea of the recipient subject and preferably allowed to 'dry in'. Positioning the overlay or composition is for instance done using surgical forceps or a spatula. A soft bandage lens is then preferably positioned onto the eye.

Hence in a preferred embodiment, a method of the invention further comprises one or more of the following steps:

rehydration of the overlay or composition;

- staining the overlay or composition with a vital dye;
- allowing the overlay or composition to dry in, e.g. for 1-60 minutes; and/or
- positioning a soft bandage lens onto the eye after the overlay or composition has been positioned onto the cornea, e.g. for 6 hours to several weeks.

As used herein "anterior corneal disorder" refers to a disorder that affects the anterior side or the cornea, i.e. the BL or anterior stromal tissue of the cornea. In a preferred embodiment, the anterior corneal disorder is selected from the group consisting of a corneal curvature disorder, a corneal instability disorder, a corneal wound healing disorder, a corneal surface disorder, a corneal defect, melt or peripheral thinning, an ocular surface disease and a refractive error of the eye. In a preferred embodiment, the disorder is keratoconus. These disorders and their advantageous treatment with a method according to the invention are explained in more detail below.

Group I. Corneal Curvature Disorders

In the treatment of corneal curvature disorders characterized by progressive steepening of the cornea, including but not limited to 1) keratoconus, and 2) post-excimer laser ectasia, for example after photorefractive keratectomy (PRK), phototherapeutic keratectomy (PTK), laser-assisted in-situ keratomileusis (LASIK) and superficial epithelial keratectomy, it is common practice to replace the central part of the cornea. To this end a penetrating keratoplasty (PK) may be performed, that is, a full-thickness, cylindrical part of the cornea is removed, including stroma, DM and endothelium, and replaced by donor tissue, or the most posterior layers may be spared when performing a deep lamellar anterior keratoplasty (DALK).

These known techniques have the disadvantage that the donor part of the cornea has to be sutured into the peripheral cornea of the patient, resulting in disorders in at least the outer surface of the cornea. This may be detrimental to the patient given the substantial risk of long term complications and/or side effects, since the technique is associated with relatively severe trauma to the cornea, suture related problems, ineffective wound healing and irregular astigmatism.

In the past decades, alternative procedures have been introduced like UV-crosslinking, the implantation of (synthetic or tissue-derived) intracorneal ring segments, and a BL as a stromal inlay. All these procedures aim to halt progression of the corneal steepening effect and/or some degree of flattening of the corneal curvature. However, UV-crosslinking and intracorneal ring segments may only be effective in relatively mild cases. Advanced cases may also be eligible for a BL stromal inlay, but this procedure is technically challenging and prone to corneal perforation during surgery, owing to the pre-existing thinning of the corneal tissue. With all of these procedures, the effect on the patient's cornea is often variable and therefore unpredictable.

For the disorders of group I, the overlay or composition in particular preferably comprise a single layer or multiple layers of a BL.

Group II. Corneal Instability Disorders

Corneal instability, including but not limited to 1) diurnal fluctuation in visual acuity after radial keratotomy surgery, 2) post-PK wound instability, etc., is another group of disorders that is difficult to manage clinically. Most often, the patient's cornea has been subjected to corneal (refractive) surgery, and as a result, the mechanical integrity of the cornea is compromised. PK, DALK, UV-crosslinking, circular sutures and other techniques have been described in these cases, most often with disappointing results, because it is not uncommon for additional interventions to worsen the situation or to introduce a different set of complications.

For the disorders of group II, the overlay or composition in particular preferably comprise a single layer or multiple layers of a BL.

Group III. Corneal Wound Healing Disorders

To manage corneal wound healing disorders, including but not limited to 1) stromal haze formation due to subepithelial fibrosis after PRK, PTK or superficial epithelial keratectomy, 2) post-infectious corneal scarring, and scarring after trauma, tissue replacement through a PK, DALK, anterior lamellar keratoplasty (ALK), re-PRK or superficial keratectomy, or amniotic membrane transplantation can be performed. Since an undesired wound healing response was the underlying cause of the complications, it is not uncommon that re-intervention aggravates the situation and that the final clinical outcome is disappointing.

For the disorders of group III, the overlay or composition may advantageously comprise a single layer or multiple layers of a BL, a DM or a crystalline lens capsule. In a preferred embodiment, the overlay or composition in particular preferably comprise a single layer or multiple layers of a BL.

Group IV. Corneal Defects, Melts, Peripheral Thinning and Surface Irregularities A large array of corneal defects and irregularities including but not limited to those after corneal refractive surgery, postinfectious disease, associated with autoimmune disorders, or that cause ignota, is currently treated with PK, DALK, anterior lamellar keratoplasty (ALK), and amniotic membrane transplantation. Most of these procedures are associated with considerable risks and/or side effects, because the underlying pathology may still be present or reoccur, often rendering the eventual clinical outcome as rather poor.

For the disorders of group IV, the overlay or composition may advantageously comprise a single layer or multiple layers of a BL, a DM or a crystalline lens capsule. In a preferred embodiment, the overlay or composition in particular preferably comprise a single layer or multiple layers of a BL.

Group V. Ocular Surface Disease

Similarly, ocular surface disease, including but not limited to epithelial defects, chemical burn, dry eye, symblepharon, pemphygoid, stem cell deficiency, etc., it is common practice to prescribe topical medication or to perform a conjunctival flap, mucosal membrane- and/or amniotic membrane transplantation. To this end, a conjunctival flap or donor membrane is sutured over the defect to allow the corneal epithelium to grow over the defect using the membrane as a scaffold. Disadvantages of an amniotic membrane transplantation is that the membranes may retract after transplantation, and that the grafts tend to dissolve within months. A conjunctival flap and mucosal membrane graft may remain in-situ, but these interventions commonly have the disadvantage of reducing the visual acuity of the eye. Alternatively, a stem cell transplantation may be performed, but the overall success rate is relatively poor and even autologous grafts may show variable outcomes.

For the disorders of group V, the overlay or composition may advantageously comprise a single layer or multiple layers of a BL, a DM or a crystalline lens capsule. In a preferred embodiment, the overlay or composition in particular preferably comprise a single layer or multiple layers of a BL.

Group VI. Refractive Error of the Eye

In the treatment of refractive errors of the eye, it is common practice to perform biological or synthetic lenticle implantation. To this end, collagen or polymer lenses can be placed under the corneal epithelium or within the stroma, or in front of the crystalline lens. Disadvantages of these techniques are that these synthetic lenses lack long-term biocompatibility or may damage the intraocular structures.

For the disorders of group VI, the overlay or composition may advantageously comprise a single layer or multiple layers of a BL, a DM or a crystalline lens capsule. In a preferred embodiment, the overlay or composition in particular preferably comprise a single layer or multiple layers of a BL. After restoration of the corneal epithelial cell layer, the overlay may then be partially ablated with excimer laser photorefractive keratectomy (PRK), to shape the overlay into a lenticule with refractive power, to obtain the desired refractive effect. Depending on the refractive error, the overlay may be produced with a specific diameter and thickness, preferably between 6-11 mm in diameter, and more preferably 7-10 mm in diameter, and preferably 10-250 um in thickness, to add sufficient tissue to enable the desired change in power, depending on the desired refractive correction. Overall, the same nomograms can be used as those for PRK on virgin corneas, although the effect of the laser, and the associated systemic error, may with the laser type and/or brand.

Features may be described herein as part of the same or separate aspects or embodiments of the present invention for the purpose of clarity and a concise description. It will be appreciated by the skilled person that the scope of the invention may include embodiments having combinations of all or some of the features described herein as part of the same or separate embodiments.

The invention will be explained in more detail in the following, non-limiting examples.

A. Epikeratophakia as described in U.S. Pat. No. 4,662,881 has been performed for at least 5 decades. The graft usually consists of donor stroma with its Bowman layer on top. Since a wound healing response is virtually absent at the donor-to-host interface (ie. at the donor stroma-to-recipient Bowman layer interface), the graft is 'tucked in' into the host stroma in the periphery, to allow for stroma-to-stroma wound healing in these areas, and therefore long term fixation of the graft.

B. From a wound healing perspective, a 'tissue contact lens' as described in US 2003/105521 A1 may be considered a type of epikeratophakia, since a wound healing response is unlikely to occur at the donor-to-host interface (i.e. at the donor stroma-to-recipient Bowman layer interface). Since the graft is not 'tucked in' in the corneal periphery, graft may remain at risk of dislocation due to a lack of wound healing induced tissue fixation.

C. An absent wound healing response at the donor-to-host interface (ie. at the recipient stroma-to-donor Bowman layer interface) may be exploited to avoid scar tissue (re)formation in the management of stromal haze after photorefractive keratectomy (PRK) by positioning a donor Bowman layer onto an post-laser ablated stromal bed, as described in Lie et al 2010. Although effective in improving the visual acuity through minimizing scar tissue formation at the interface, the graft may remain at risk of dislocation because of the lack of wound healing induced tissue fixation.

D. Procedure according to the present invention. In contrast to the absence of a wound healing response at the donor-to-host interface (ie. at a stroma-to-Bowman layer interface), wound healing does occur if a donor Bowman layer is positioned onto the recipient anatomical Bowman layer, thereby providing long term tissue fixation.

Figure 1:
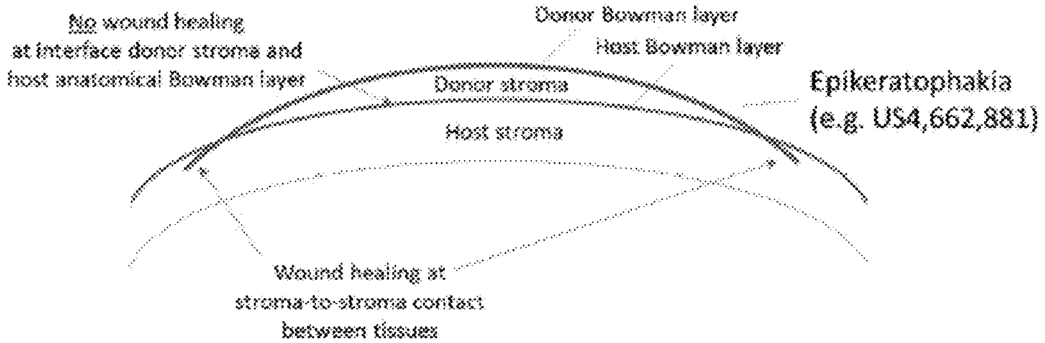
FIG. 1: comparison of prior published procedures and the procedure of the present invention.
Figure 1:
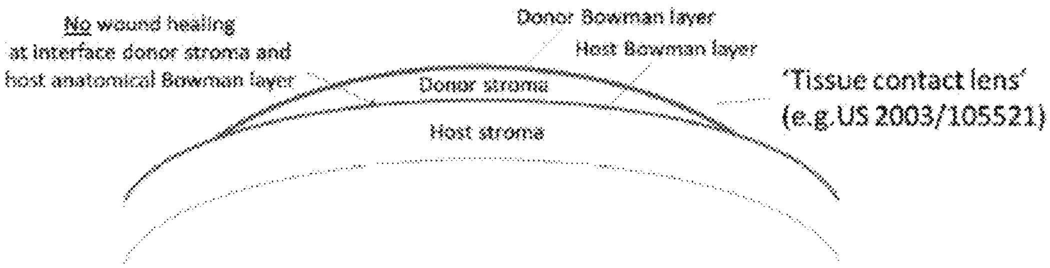
Figure 1:
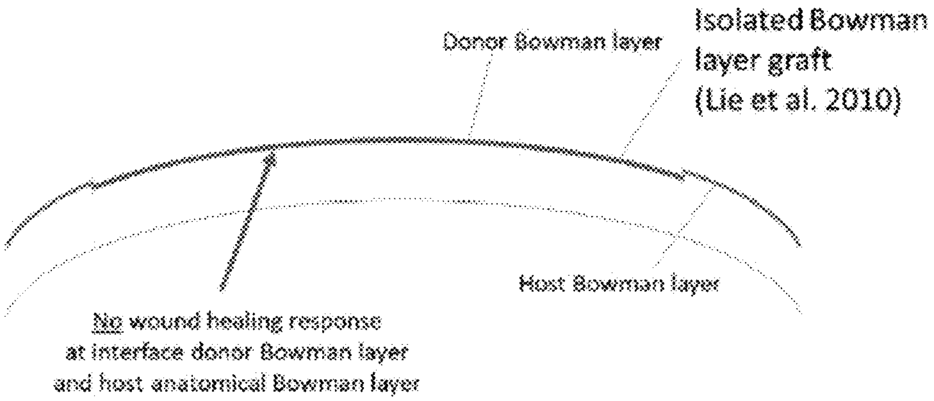
Figure 1:
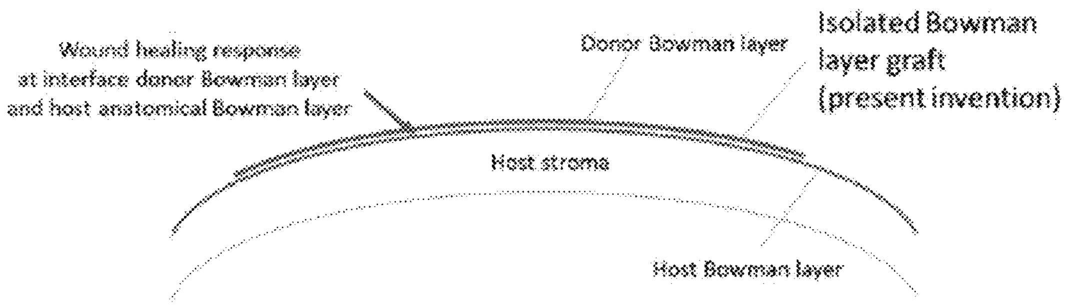
Figure 2:
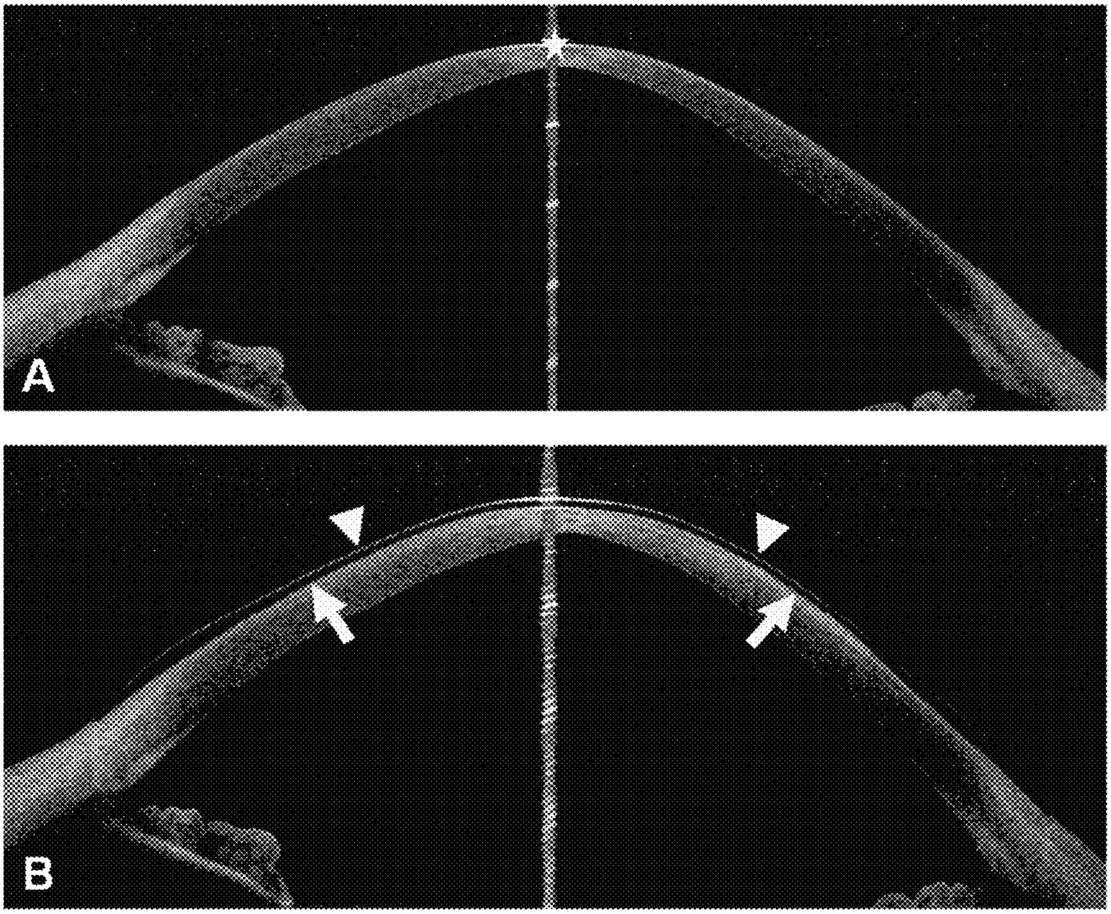
Figure 2:
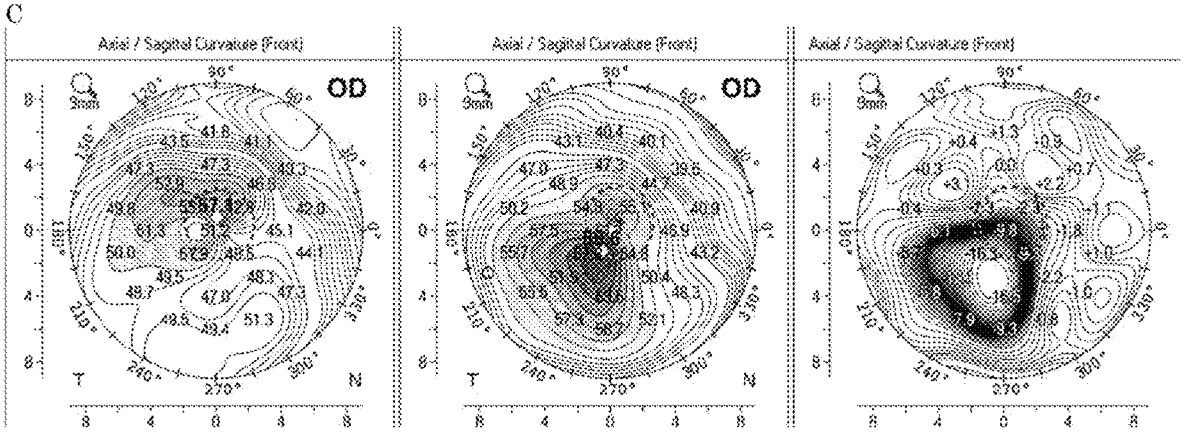

FIG. 2: Scheimpflug images of a cornea before (A) and six months after (B) a BL overlay (arrows) in a patient with advanced keratoconus (asterix). The arrowheads point to the contact lens that is in-situ over the BL overlay. (C) Pentacam topography maps, pre- (middle), postoperative (left) and difference map (right), of the same cornea at, show up to 15-16 diopters in corneal flattening.

Figure 3:
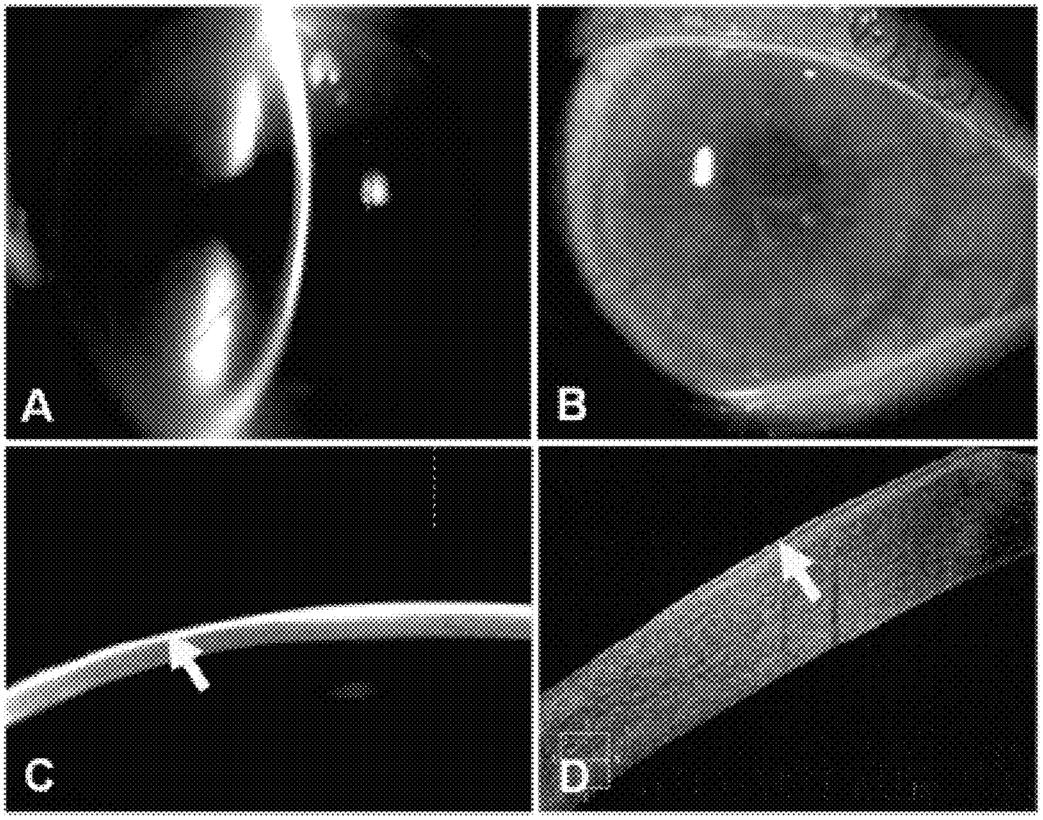
Figure 3:
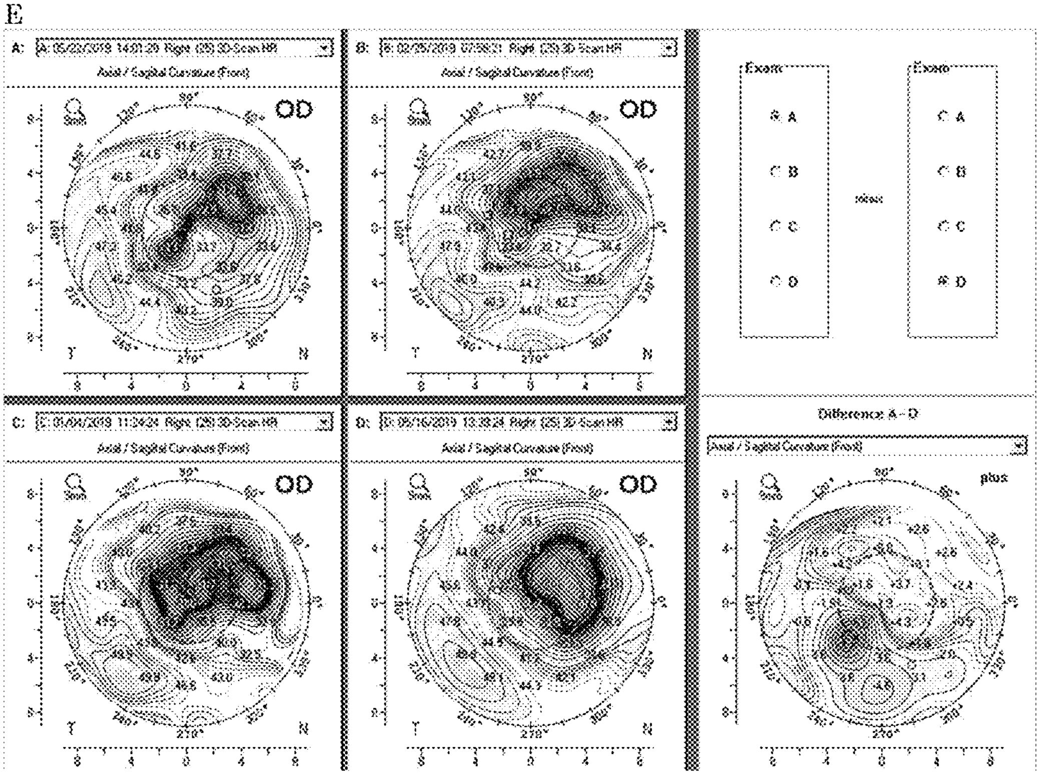

FIG. 3: Slit-lamp images (A & B), Scheimpflug image (C) and AC-OCT image (D) two weeks after a BL overlay (arrows) in an eye with diurnal variation in visual acuity resulting from refractive fluctuation owing to corneal instability after radial keratotomy surgery. (E) Pentacam topography maps pre-operatively and up to one year postoperatively, of a cornea after a BL overlay in the same patient. Note the more regular topography over time.

Figure 4:
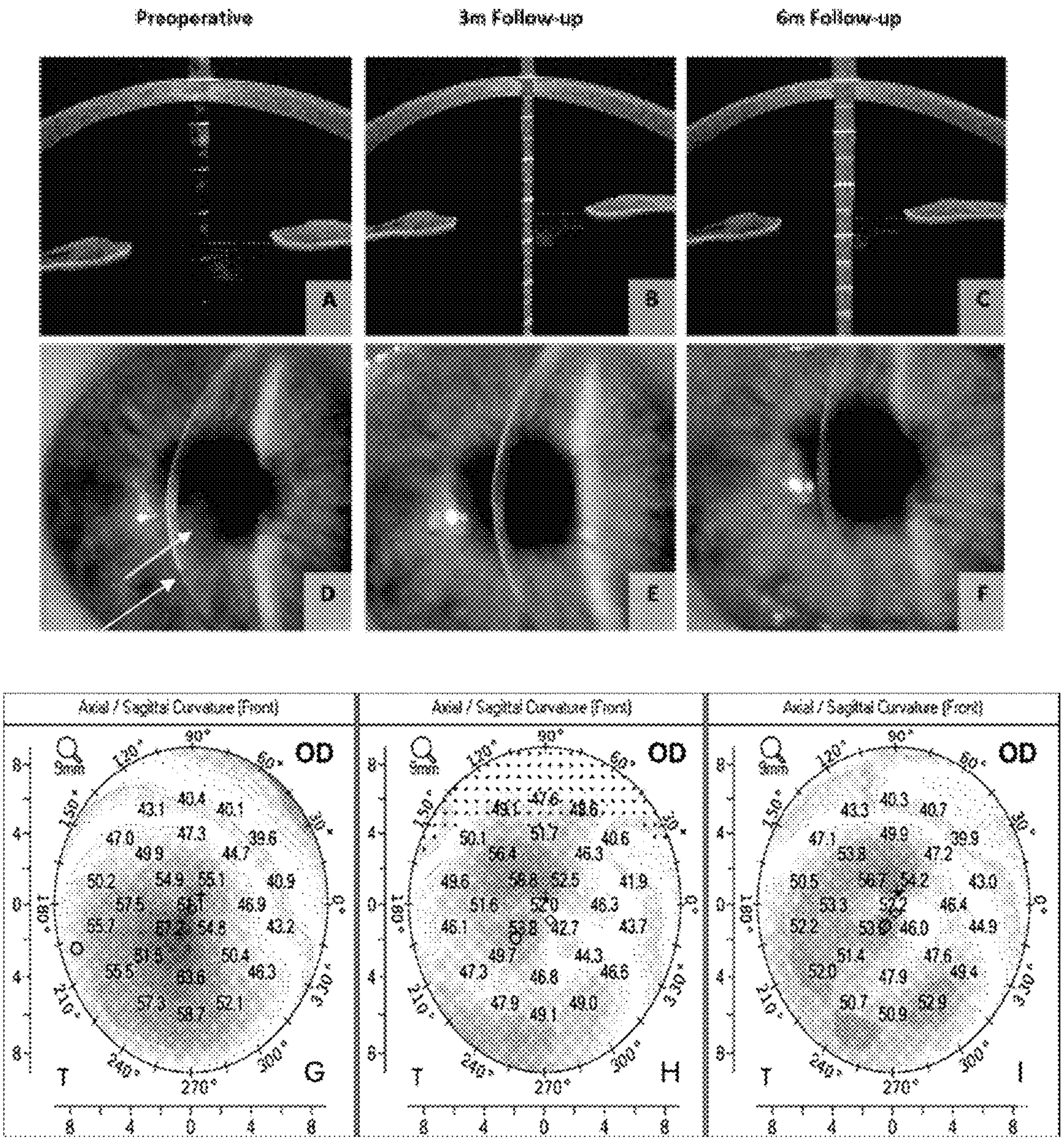

FIG. 4: An eye that underwent isolated Bowman layer overlaying in accordance with the present invention, before and at 3 and 6 months after surgery. Note the flattening effect from Kmax 67D (G) to 58D (H) to 56D (I), attributed to wound healing induced tissue contraction and fixation. The central cornea also shows remodeling displayed by less reflective tissue (A-C) and improving central corneal clarity (D-F). In addition, the eye shows a white opacities preoperative of stromal scare tissue (see white arrow in D), that disappears after surgery.

Figure 5:
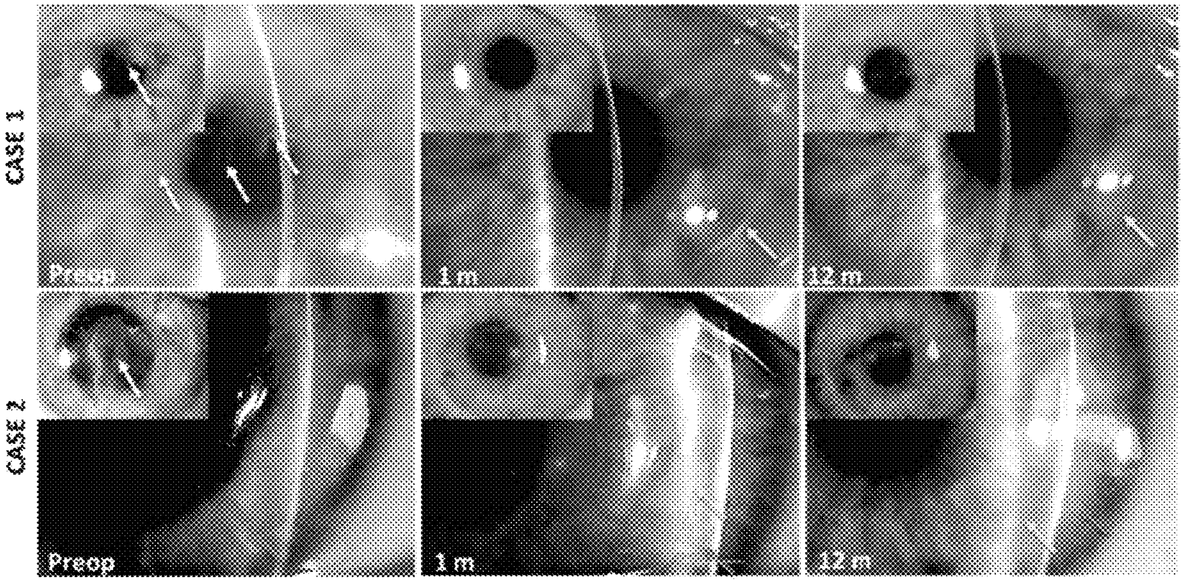

FIG. 5: Slit-lamp images of two cases, before and at 1 month and at 12 months after BL onlay grafting for herpetic scarring. Note the superficial anterior central opacities of the cornea preoperatively (white arrows). Postoperatively, the cornea became relatively smoother and more transparent, and the BL was completely integrated and epithelialized, being only visible at its far edges (light grey arrows in 1 m and 12 m images).

EXAMPLES

Case 1:

In the treatment of corneal curvature disorders (Group I), it was found that the donor tissue overlay was effective in 1) reducing the steepened corneal curvature up to 20 diopters and 2) stabilizing the keratoconus, that is, to halt progression (FIG. 2).

An eye with advanced keratoconus (>70 diopters) had a 9.0 mm single-layer BL overlay positioned onto the host remnant BL under topical anesthesia. Six months later, the cornea showed up to 15-16 diopters of flattening of the anterior corneal surface and thereafter, topography images appeared stable over time (FIG. 2).

If desired, a multi-layered donor tissue overlay can be used and/or the procedure can be repeated, to obtain a stronger initial effect or a cumulative effect, since advanced keratoconic corneas may show steepening up to more than 80 diopters (while a non-keratoconic cornea curvature averages to about 43 diopters).

Case 2:

In the management of corneal instability disorders (Group II), a similar approach was found to be effective in stabilizing the cornea and therefore to reduce the diurnal fluctuation in refractive error (FIG. 3). Commonly a single layer donor tissue overlay was sufficient to obtain the desired clinical effect.

An eye with diurnal fluctuation in visual acuity >25 years after radial keratotomy surgery had a 8.0 mm single BL overlay positioned onto the (previously incised) host BL under topical anesthesia. At one month, the diurnal fluctuation in visual acuity had subjectively diminished to acceptable levels and topography imaging showed a mild steepening of the cornea up to one year (FIG. 3).

Further Patient Examples (Cases 3-9) and Potential Clinical Applications:

In corneal wound healing disorders, defects, melts, peripheral thinning, surface irregularities, and ocular surface disease (Groups III, IV and V), a donor tissue overlay was found to be clinically effective in most cases. Both these groups cover a wide range of pathology. In general, a donor tissue overlay showed excellent results in cases without active inflammation, such as haze or scarring after excimer laser surgery and a postinfectious scar in the quiet phase. In contrast to other methods currently available, the donor tissue overlay was found not to dissolve over time.

The donor tissue overlay can also be used to manage refractive errors of the eye by using a single or most commonly a multi-layered overlay that is allowed to stay in-situ for several weeks to let the epithelium grow over. The overlay may then be tuned up by using excimer laser photoablation, so that the corneal curvature is re-shaped similarly to a virgin cornea undergoing excimer laser surgery, with a treatment range from approximately +6 to −12 diopters, or more preferably from +4 to −6 diopters. The major advantage of remodeling a donor tissue overlay instead of the patient's own cornea, is that the procedure allow for a curvature change without compromising the patient's cornea itself, so that the procedure can be 'undone' if desired (for example if the final result is disappointing), to return the pre-operative situation.

Case 3: An eye with moderate keratoconus (about 55 diopters) had a 9.0 mm multi-layer BL overlay positioned onto the host remnant BL under topical anesthesia. Six months later, the cornea showed up to 11 diopters of flattening of the anterior corneal surface and thereafter, topography images appeared stable over time.

Case 4: An eye with post-excimer laser (LASIK) ectasia (about 50 diopters) had a 9.0 mm single BL overlay positioned onto the host BL under topical anesthesia. Three months later, the cornea showed up to 5 diopters of flattening of the anterior corneal surface and thereafter, topography images appeared stable over time.

Case 5: An eye with wound dehiscence >15 years after penetrating keratoplasty had a 9.0 mm single BL overlay positioned onto the central graft under local anesthesia. At six months, topography imaging showed a more regular anterior corneal surface (K-value re-distribution).

Case 6: An eye with a post-infectious ocular herpes simplex scar in the quiet phase had a single BL overlay positioned onto the central cornea under local anesthesia. Postoperatively, slit-lamp imaging showed a slow diminution of the opacity, up to 2 years.

Case 7: In an eye with a subepithelial scar (haze grade 4) after PRK, a superficial keratectomy was performed after positioning a single BL overlay across the cornea under local anesthesia. Postoperatively, no recurrence of the scar was observed up to 8 years.

Case 8: In an eye with a −2 diopter refractive error, a multilayered BL overlay was positioned onto cornea under local anesthesia. After six months, a PRK was done using routine nomograms to correct the refractive error, that is to flatten the anterior corneal curvature (reduce the corneal power).

Case 9: An eye that underwent isolated Bowman layer overlaying in accordance with the present invention to treat keratoconus, before and at 3 and 6 months after surgery (FIG. 4). Note the flattening effect from Kmax 67D (FIG. 4G) to 58D (FIG. 4H) to 56D (FIG. 4I), attributed to wound healing induced tissue contraction and fixation. The central cornea also shows remodeling displayed by less reflective tissue (FIG. 4A-C) and improving central corneal clarity (FIG. 4D-F). In addition wound healing in the underlying stromal tissue resulted in mitigation and/or disappearance of stromal scar tissue (response), preoperatively visible as a white opacity in FIG. 4D.

Cases 10 and 11:

Two cases of herpetic scarring that underwent isolated Bowman layer overlaying in accordance with the present invention. Eyes of both cases showed a denser scar (see white arrows in FIG. 5 preoperatively). The depth of the scar was 150 and 130 mm approximately, respectively for case 1 and case 2, as measured with anterior segment optical coherence tomography.

BL onlay grafting was performed in both cases. From a donor globe obtained less than 36 hours postmortem, a corneoscleral button was excised, the endothelium (if viable) was AQ:3 peeled off to be used for DMEK surgery, and the remaining anterior button was mounted on a custom-made holder. The donor BL was stripped from the anterior stroma with modified McPherson forceps so that a BL sheet was obtained.9 The BL formed a roll spontaneously and was stored in an organ culture medium until the time of transplantation.

The surgery was performed under retrobulbar anesthesia. The recipient epithelium was removed from the corneal surface by using surgical sponges and a hockey stick knife. The stromal bed was then irrigated to remove calcium and epithelial remnants. The most superficial corneal rests of subepithelial fibrosis were then gently debrided using a hockey stick knife. Once the corneal surface was as smooth as possible, a BL graft (9.0 mm in case 1 and 8.5 mm in case 2) stained with 0.06% trypan blue solution (VisionBlue; DORC International, Zuidland, Netherlands) was carefully positioned (epithelial side up) without folds onto the recipient cornea and allowed to dry. Amniotic membrane was then sutured covering the cornea to improve postoperative reepithelialization, and a soft bandage lens was placed on the eye.

After surgery, a well-integrated BL graft was observed in both cases, completely epithelialized and without signs of decentration or dislocation. Complete and rapid reepithelialization was seen along with a steady improvement of the corneal clarity and relative "smoothening" of the anterior corneal surface. Postoperatively, a steady improvement in the corneal clarity was observed, when compared with the preoperative state. Throughout the follow-up period (12 months), the corneal opacity did not recur. The presence of the BL graft could be confirmed on slitlamp biomicroscopy and anterior segment optical coherence tomography, by the outer edges and a faint line underneath the epithelium (FIG. 5).

REFERENCES

Birbal R S, Ni Dhubhghaill S, Bourgonje V J A, Hanko J, Ham L, Jager M J, Boehringer S, Oellerich S, Melles G R J. Five-year graft survival and clinical outcomes of 500 consecutive cases after Descemet membrane endothelial keratoplasty. Cornea. 2019. Accepted (status September 2019).

Groeneveld-van Beek E A, Parker J, Lie J T, Bourgonje V, Ham L, van Dijk K, van der Wees J, Melles G R. Donor Tissue Preparation for Bowman Layer Transplantation. Cornea. 2016 December; 35(12):1499-1502.

Lie J, Droutsas K, Ham L, Dapena I, Ververs B, Otten H, van der Wees J, Melles G R. Isolated Bowman layer transplantation to manage persistent subepithelial haze after excimer laser surface ablation. J Cataract Refract Surg. 2010 June; 36(6):1036-41.

Melles G R, Wijdh R H, Nieuwendaal C P. A technique to excise the descemet membrane from a recipient cornea (descemetorhexis). Cornea. 2004; 23:286-8.

Melles G R J, Ong S, Ververs B, Van der Wees J. Descemet membrane endothelial keratoplasty (DMEK). Cornea 2006; 25:987-90.

Parker J S, van Dijk K, Melles G R. Treatment options for advanced keratoconus: A review. Sury Ophthalmol. 2015 September-October; 60(5):459-80.

Parker J S, Huls F, Cooper E, Graves P, Groeneveld-van Beek E A, Lie J, Melles G R J. Technical feasibility of isolated Bowman layer graft preparation by femtosecond laser: a pilot study. Eur J Ophthalmol. 2017 Nov. 8; 27(6):675-677.

Sharma B, Dubey A, Prakash G, Vajpayee R B. Bowman's layer transplantation: evidence to date. Clin Ophthalmol. 2018 Mar. 5; 12:433-437.

Spinozzi D, Miron A, Bruinsma M, Dapena I, Lavy I, Binder P, Rafat M, Oellerich S, Melles G R J. Evaluation of the suitability of biocompatible carriers as artificial transplants using cultured porcine corneal endothelial cells. Curr Eye Res 2019; 44:243-9.

van Dijk K, Parker J, Tong C M, Ham L, Lie J T, Groeneveld-van Beek E A, Melles G R. Midstromal isolated Bowman layer graft for reduction of advanced keratoconus: a technique to postpone penetrating or deep anterior lamellar keratoplasty. JAMA Ophthalmol. 2014 Apr. 1; 132(4):495-501.

van Dijk K, Liarakos V S, Parker J, Ham L, Lie J T, Groeneveld-van Beek E A, Melles G R. Bowman layer transplantation to reduce and stabilize progressive, advanced keratoconus. Ophthalmology. 2015 May; 122 (5):909-17.

The invention claimed is:

1. A method for the treatment or alleviation of an anterior corneal disorder in a subject in need thereof, the method comprising:

removing corneal epithelial cells from an eye of said subject without removing any corneal tissue or other ocular tissue located posterior to the corneal epithelial cell layer; and positioning an overlay consisting of a Bowman layer (BL) or consisting of more than one BL, on the anterior surface of said corneal tissue located posterior to the corneal epithelial cell layer.

2. The method according to claim 1, wherein a tissue remodeling response is induced in corneal stroma of the subject, wherein said corneal stroma comprises scar tissue associated with or resulting from the anterior corneal disorder.

3. The method according to claim 1, wherein said corneal tissue located posterior to the corneal epithelial cell layer comprises a BL or part of a BL and anterior corneal stromal tissue.

4. The method according to claim 1, wherein said overlay is positioned sutureless on said corneal tissue.

5. The method according to claim 1, wherein said overlay has an average thickness of 7-600 μm and/or has an average diameter of 1-12 mm.

6. The method according to claim 1, wherein at least 80% of corneal epithelial cells covering the part of the anterior surface of the corneal tissue that will be covered by the overlay is removed from the eye of said subject.

7. The method according to claim 1, wherein said overlay consists of one or more donor BLs.

8. The method according to claim 7, wherein said one or more donor BLs is or are selected from the group consisting of human or animal BL or BLs.

9. The method according to claim 1 wherein said treatment or alleviation comprises inducing a wound healing response at the interface between said overlay and the Bowman layer of the subject and/or a tissue remodeling response in the corneal stroma of the subject.

10. The method according to claim 1 wherein said overlay or said BL is treated with a substance selected from the group consisting of dyes, riboflavin, adjuvants that facilitate visualization and active components.

11. The method according to claim 10, wherein said active component is selected from the group consisting of stromal growth factors, epithelial growth factors and any combination thereof.

12. The method according to claim 1, wherein the cornea of said subject comprises at least part of a BL.

13. The method according to claim 12, wherein said part of a BL comprises at least 10% of an intact Bowman's layer.

14. The method according to claim 1, wherein said method further comprises allowing the overlay to dry in and/or positioning a soft bandage lens onto the eye.

15. The method according to claim 1, wherein said overlay is stained before said overlay is positioned on the anterior surface of said corneal tissue located posterior to the corneal epithelial cell layer.

16. The method according to claim 15, wherein said overlay is stained with a vital dye.

17. The method according to claim 1, wherein said anterior corneal disorder is selected from the group consisting of a corneal curvature disorder, a corneal instability disorder, a corneal wound healing disorder, a corneal surface disorder, a corneal defect, melt or peripheral thinning, an ocular surface disease and a refractive error of the eye.

18. The method according to claim 1, wherein the overlay is a composition consisting of more than one layer, wherein each layer independently consist of a Bowman layer (BL).

19. The method according to claim 1, wherein the cornea of the subject lacks a BL and wherein said corneal tissue located posterior to the corneal epithelial cell layer comprises anterior corneal stroma.

* * * * *